United States Patent
Lüghausen et al.

(10) Patent No.: US 9,528,948 B2
(45) Date of Patent: Dec. 27, 2016

(54) METHOD AND DEVICE FOR DETECTING THE STRUCTURE OF MOVING SINGLE ITEMS, IN PARTICULAR FOR DETECTING FOREIGN PARTICLES IN LIQUID OR PASTE-LIKE PRODUCTS

(71) Applicant: Wipotec Wiege-und Positioniersysteme GmbH, Kaiserslautern (DE)

(72) Inventors: Kai Mark Lüghausen, Alzey (DE); Theodor Doll, Bochum (DE)

(73) Assignee: Wipotec Wiege- und Positioniersysteme GmbH, Kaiserslautern (DE)

( * ) Notice: Subject to any disclaimer, the term of this patent is extended or adjusted under 35 U.S.C. 154(b) by 227 days.

(21) Appl. No.: 14/348,049

(22) PCT Filed: Sep. 25, 2012

(86) PCT No.: PCT/DE2012/100300
§ 371 (c)(1),
(2) Date: Jul. 14, 2014

(87) PCT Pub. No.: WO2013/044910
PCT Pub. Date: Apr. 4, 2013

(65) Prior Publication Data
US 2014/0328463 A1 Nov. 6, 2014

(30) Foreign Application Priority Data
Sep. 27, 2011 (DE) .................. 10 2011 053 971

(51) Int. Cl.
*G21K 5/10* (2006.01)
*G01N 23/04* (2006.01)

(52) U.S. Cl.
CPC ......... *G01N 23/04* (2013.01); *G01N 2223/635* (2013.01); *G01N 2223/643* (2013.01)

(58) Field of Classification Search
CPC ...... G01N 23/04; G01N 23/06; G01N 23/083; G01N 23/087; G01N 23/12; G21K 5/10
(Continued)

(56) References Cited

U.S. PATENT DOCUMENTS

| 3,665,184 A | 5/1972 | Schagen |
| 5,020,085 A | 5/1991 | Kawara et al. |

(Continued)

FOREIGN PATENT DOCUMENTS

| CN | 101455573 A | 6/2009 |
| JP | 2004257884 A | 9/2004 |

(Continued)

OTHER PUBLICATIONS

Japanese Patent Office Notification of Reasons for Refusal, Japanese Patent Application No. 2014-532248, May 22, 2015.
(Continued)

*Primary Examiner* — Jurie Yun
(74) *Attorney, Agent, or Firm* — The Culbertson Group, P.C.

(57) ABSTRACT

A method includes directing a broadband X-ray emission along a predetermined fixed detection line across a direction of travel of an object and detecting the X-rays at several sampling positions of the object relative to the detection line. Sensors making up the detection line simultaneously detect a first partial image for a first spectral segment of the X-ray and a second partial image for a second spectral segment or the entire spectrum of the X-ray. In order to generate the relevant partial image data, a value of the radiation energy in the relevant spectral segment is determined at each detection position associated with a partial image. The partial image data of the first and second image are arith-
(Continued)

metically combined into a partial output image, and the partial output images of all sampling positions are combined into one output image.

16 Claims, 4 Drawing Sheets

(58) Field of Classification Search
USPC .............................. 378/53, 62, 156, 158, 69
See application file for complete search history.

(56) References Cited

U.S. PATENT DOCUMENTS

| | | | |
|---|---|---|---|
| 5,841,832 A | 11/1998 | Mazess et al. | |
| 6,332,015 B1 | 12/2001 | Honda | |
| 6,370,223 B1 | 4/2002 | Gleason et al. | |
| 6,567,496 B1 * | 5/2003 | Sychev | G01N 23/04 378/57 |
| 7,426,260 B2 * | 9/2008 | Cantu | G01T 1/295 250/370.11 |
| 7,970,096 B2 | 6/2011 | Pavlovich et al. | |
| 8,223,922 B2 * | 7/2012 | Suyama | G01N 23/04 250/370.09 |
| 2008/0247504 A1 | 10/2008 | Edic et al. | |
| 2009/0147910 A1 | 6/2009 | Edic et al. | |
| 2010/0119040 A1 | 5/2010 | Suyama et al. | |
| 2010/0278296 A1 | 11/2010 | Edic et al. | |

FOREIGN PATENT DOCUMENTS

| | | |
|---|---|---|
| JP | 2007127611 A | 5/2007 |
| JP | 2010117172 A | 5/2010 |
| JP | 2010172590 A | 8/2010 |
| WO | 9733160 A1 | 9/1997 |
| WO | 0127601 A1 | 4/2001 |
| WO | 2009073284 A1 | 6/2009 |
| WO | 2010100274 A2 | 9/2010 |

OTHER PUBLICATIONS

PCT, International Search Report for PCT/DE2012/100300 issued on Oct. 15, 2013 (5 pages).
PCT, Written Opinion for PCT/DE2012/100300 issued on Oct. 15, 2013 (13 pages).

* cited by examiner

METHOD AND DEVICE FOR DETECTING THE STRUCTURE OF MOVING SINGLE ITEMS, IN PARTICULAR FOR DETECTING FOREIGN PARTICLES IN LIQUID OR PASTE-LIKE PRODUCTS

TECHNICAL FIELD OF THE INVENTION

The invention concerns a method for detecting the structure of moving objects, in particular for detecting foreign particles in liquid or paste-like products. The invention also encompasses a corresponding device.

BACKGROUND OF THE INVENTION

Noninvasive or nondestructive inspection of objects may be accomplished by irradiating the objects with X-rays and collecting an X-ray image by means of a suitable detector. To bring out specific characteristics or structures of an object, the dual energy method is used, with which the object is irradiated with X-rays at two different energy spectra (or frequency or wavelength spectra) and one image is registered for each of the two spectra. This utilizes the effect that certain materials or material structures exhibit different absorption or attenuation behaviors for radiation at different wavelengths or frequencies. The two images can then be combined by computer to improve the ability to detect certain structures. For example, a difference image can be generated by combining the image data, which are preferably in digital form, pixel by pixel, by a weighted subtraction. The output image can then be tested either visually or by means of a pattern recognition method to see whether certain criteria are satisfied. For example, this allows foreign objects in liquid or paste-like products to be detected more reliably than would be possible in the case of radiation with a single narrow band or with a broadband X-ray (for example, DE 690 11 194 T2).

However, this dual energy process, which can also be designed as a multi-energy process if more than two X-rays that differ in wavelength or frequency or energy spectrum are used, results in a higher cost than irradiation with one X-ray that has only a single, constant spectrum.

The dual energy method or multi-energy method is known in a number of variations. For example, two or more radiation sources that have different spectral characteristics can be used. They can be combined in each case with one detector, or a corresponding number of detectors. For example, U.S. Pat. No. 6,370,223 B1 shows a device with two radiation sources and two detectors, where each pair consisting of a radiation source and associated detector is situated at different positions on a conveyor belt for transporting objects that are to be inspected. However, this also results in a double expense for hardware to generate the two images for irradiation with different energy spectra.

Also known is the use of one or more filters (especially edge filters) in order to generate, from a broadband source, a beam with only a portion of the original spectrum and the use of the same detector for each image acquisition (for example, U.S. Pat. No. 3,665,184).

It is also possible to control one and the same X-ray source differently at successive points in time so that not only is the radiation power (constant over the entire spectrum) altered, but a change of the spectral characteristic is also achieved (JP 2010172590A).

However, these methods are hardly applicable for rapidly moving objects when only one detector is used, since it is not possible to generate images for identical parts of the object or indeed the entire object practically simultaneously at justifiable expense. For this, one would have to use extremely fast detector devices in order to register the at least two images for the different radiation spectra as closely as possible to each other in succession. In addition, the switching from the one radiation source to the other would also have to take place correspondingly rapidly. The solution of using a flat panel detector and bringing images acquired at short time intervals, which thus are spatially shifted on the detector, into alignment by computer means, would also result in a corresponding expense. Such flat panel detectors, which are mostly made as digital detectors with pixels arranged in a matrix pattern, are relatively expensive and if the resolution is high and exposure time is short, also lead to only low radiation energy being detected per pixel. Noise problems can arise because of this.

A dual energy method for investigation of the human body is known from CN 101455573 A, in which a spatial filter is placed immediately before a flat panel sensor. The spatial filter has strips of two different types, which are alternately arranged. The different strip types have materials that have different densities in the irradiation direction. The different filter regions act so that, in one of the strip-shaped regions, the radiation is not dampened or is only weakly dampened, and in the other of the strip-shaped regions, a (stronger) filter effect (high pass, low pass or band pass filter effect) exists, or a different edge filter effect exists in each of the two regions. This allows two images of the same object that contain different information to be generated simultaneously, with a single exposure. These images can then be combined by computer. Here, the complete image information (in the required resolution) can also be calculated in the total cross section (Nyquist-Shannon sampling theorem) with a single arrangement of strips, if the local sampling interval generated across the lengthwise direction of the strips is small enough that a structure to be imaged, which has a specified minimum size (in the transverse direction), is sampled at least twice. This can take place, for example, through interpolation processes or by means of a fast Fourier transform. The calculated image information can then be combined by a sign-dependent addition, and a weighted subtraction of the two images can, of course, also be realized. Through this, the advantage of the dual energy method can be combined with the advantage of using a single detector and a single radiation source (a broadband source or one with at least two narrow-band energy regions).

The method described in CN 101455573 A and the corresponding device are not well suited for use in an industrial process, for example for quality control of products, where it is often necessary to detect the internal and/or external structure of rapidly moving products. In particular, the use of a sufficiently large flat panel detector with sufficient resolution in industrial use would be much too costly.

SUMMARY OF THE INVENTION

The present invention provides a method for detecting the structure of moving objects, in particular for detecting foreign particles in liquid or paste-like products. The method can be realized simply and inexpensively in an industrial process and enables a sufficiently precise inspection of rapidly moving objects. In addition, the invention also includes a corresponding device for detecting structures such as foreign particles in rapidly moving objects.

The invention employees filters similarly to the method described in CN 101455573 A for use in the medical field.

However, the invention employs a filter arrangement with a linear detector, which comprises one or more (a few) lines. Very inexpensive hardware for realization of the method can be created by using only one linear detector or a few lines of linear detectors. Embodiments of the invention may employ a single broadband X-ray source or one with at least two narrow band regions in the energy spectrum and only a single detector device, which detects the X-ray energy passing through the rapidly moving object in different spectral regions (of the energy spectrum) in one or more relatively few (for example 128) lines. The detector device has a strip spatial filter, with which two strip-shaped images of the measured object are generated for different regions of the energy spectrum of the incident X-ray on the one or the few detector lines or detection lines. This allows two line-shaped images of the imaged object to be obtained at the same time. The exposure time can be determined by the integration time for the radiation power at the location of the detection line, i.e., by the time between the clearing or reading of the image data of the relevant lines and the following time point of the reading of the newly obtained image data. The "exposure time" or the time between reading the information of two successive "line data" also determines the maximum sampling rate or the time-wise or location-wise sampling interval for the "slice by slice" sampling of the object.

Said line data is divided into at least two partial images (dual energy method) or into a plurality of partial images (multi-energy method), where each partial image is associated with the data of the detection positions within the relevant line in which the incident radiation of a spectral region of the energy spectrum associated with the partial image is detected. These detection positions are defined by the two types (dual energy method) or plurality of types (multi-energy method) of strips of the strip spatial filter. Here, it is not absolutely necessary that there be only one detector pixel present per detection position. Rather, a number of pixels of the detector of the X-ray detection device can be assigned to a single detection position along the detection line. In accordance with the invention, the course of the strips of the spatial filter, which are linear and preferably of the same width and equidistant from each other, is parallel to the direction of travel of the object, whereas the one or the plurality of detection lines are provided transverse to the direction of travel (and essentially perpendicular to the direction of irradiation). If a conveyor belt is used to transport the object, the direction of irradiation can preferably be selected to be perpendicular to the plane of the conveyor belt on which the irradiated object lies.

In this way, the object can be sampled line by line in the direction of its travel, where two different sets of the image data are obtained per line and sampling location point or sampling time point. The partial images or partial image data (preferably in digitized form) for all detection positions on which the energy spectrum can be detected are combined by computer into a partial output image. It can then be tested for the presence of specified characteristics, for example, problematic structures that are to be detected.

However, it is also possible to first combine all partial output images (or the corresponding image data) for all sampling positions into an output image, which preferably is then in the form of a digital image and which in turn can be tested for the occurrence of predetermined characteristics.

The testing of the partial output images or the output image determined therefrom can be performed by an automated evaluation system, for example an image evaluation process, or by a visual representation of the image data of the partial output image, which is visually checked by an operator.

It should be noted in general that, in accordance with the invention, any kind of high-energy radiation can be used instead of X-rays.

According to the preferred embodiment of the invention, the detection positions of a partial image along the relevant line are chosen to be equidistant and spaced so that a structure of the object that is to be detected that has a predetermined minimum dimension along the at least one line extends over at least two detection positions of said partial image. This condition results from the sampling theorem (Nyquist-Shannon sampling theorem), which says that the original signal (here the radiation distribution before the spatial filter in the relevant spectral region) from the sampled signal (the partial image for the relevant spectral region after the spatial filter) can be correctly reproduced without losses (without loss of information) only if there are no frequency components in the sampled signal that are smaller than half the sampling frequency (here: spatial sampling frequency along the detection line).

Preferably, in accordance with the method of the invention, the sampling theorem is also satisfied for the sampling of the object in its direction of travel, i.e., the sampling positions in the direction of travel of the object are then preferably equidistant and spaced so that a structure of the object to be detected with a predetermined minimum dimension in the direction of travel extends across at least two sampling positions.

If this condition is satisfied for sampling in a line and sampling in the direction of travel of the object, in each case it is possible to determine a complete output image (in a plane perpendicular to the direction of radiation at any position) that does not have any losses (with respect to the predetermined spatial resolution), in spite of the use of the strip spatial filter.

According to one embodiment of the method of the invention, the values of the relevant partial image are calculated at selected or at all detection positions of at least one more of the at least two partial images from the detected partial images of one of the at least two partial images. In this way, a partial output image that has higher resolution than the individual partial images can be calculated from the detected and calculated partial image data of two or more of the partial images. For this, two or more of the "interpolated" partial images, each of which consists of detected and calculated partial image data, can be combined into the partial output image by a weighted, sign-dependent addition of the partial image data (for identical positions in each case).

Finally, the output image can be compiled or calculated from the calculated image data for the partial output images. The calculation can also be undertaken so that the image data can also be calculated from the partial output images at positions in the direction of travel that lie between the sampling positions. As noted above, correct (lossless for the required spatial resolution) results can be achieved here if the sampling theorem is satisfied in the sampling in the direction of travel.

Of course, the data in positions between two lines (between two sampling positions) can first be calculated from the partial images for sampling along one line and only then does a compilation (weighted, sign-dependent addition of the calculated partial image data) to a complete output image take place.

In accordance with the invention, each partial output image or the complete output image or predetermined segments of the output image can then be tested for the presence of problematic characteristics that are to be detected, preferably using a pattern recognition method.

According to the preferred embodiment of the method of the invention, there are at least two detection lines, which have a predetermined spacing in the direction of travel, so that the detection positions of the at least two detection lines that are associated with one partial image are arranged equally along each line. The position and direction of each additional detection line can be generated by shifting a first detection line in the direction of travel.

In this embodiment, the X-ray can be detected at the at least two detection lines during a detection interval in a time-shifted manner so that, during each detection interval, radiation is detected that has penetrated the object essentially on the same path. This method is known as the TDI (Timing Delay Integration) method. If using a plurality of parallel detection lines, which preferably have only a small spacing (which, however, is not absolutely necessary for conducting the method), the result is a quasi "co-travelling" detection line.

Such digital TDI image detectors are known. In this case, the charge generated during one "exposure phase" or sampling phase on the individual sensor pixels of a line (detection line) after completion of the sampling phase is shifted to the relevant sensor pixels of the next (in the direction of motion) line (detection line). During the next "exposure phase" or sampling phase, a charge corresponding to the additional radiation energy occurring in said phase is added to these pixels, so that there is an integration of the amount of charge that corresponds to the sum of the radiation energy detected in all sampling phases or sampling positions. If the velocity of the "virtual co-travel" of the detection line is synchronized with the travel velocity of the object, only radiation that has penetrated the object on the same path is detected in each position of the co-travelling detection line. This corresponds to the detection of the data of a "multiply exposed" "slice" of the object as it travels.

X-ray sources for a device in accordance with the invention can be a broadband source or a source that has two or more bands in the energy spectrum. It can also be operated continuously; pulsed control is not necessary.

A spectral detection characteristic at the detection positions of a detection line that are associated with a partial image that is to be detected for a given spectral segment of the energy spectrum or the entire spectrum of the received radiation can, as noted above, be generated by means of a spatial filter. Said spatial filter can be a separate component with a strip-like structure, where the various types of preferably alternatingly arranged strips have different edge filter effects (one type of strip can even transmit the radiation uniformly dampened in the entire energy spectrum). Such a filter structure can also be made integral with the sensor, for example, as a layer with strips that have different transmission characteristics applied to a line-shaped or matrix-shaped sensor chip. The application of the layer can take place, for example, by bonding a film-like filter to the chip.

According to one embodiment of the invention, a separately made spatial filter can also be integrated into the belt of a conveyor belt, or the entire belt can be made as a spatial filter.

It is also possible to convert the X-ray to electromagnetic radiation in the optical (visible or near IR or UV) region by means of a so-called scintillator, which likewise can be made as a separate component or made integral with the spatial filter or integral with a sensor chip, and to detect said optical radiation by means of inexpensive optical detectors.

So that a strip spatial filter can also be realized by making a scintillator with different types of strips, each of which has different scintillation properties, an electromagnetic radiation is generated in the optical region, for example, only for certain segments of the energy spectrum of the incident radiation. The different types of strips can also be generated on or within different carriers (for example films), which are then bonded to each other, preferably glued. The strips of different types can then also be arranged in different planes (looking in the direction of radiation).

According to another alternative, the strip forming agents can also be generated by using a detector that has different detection characteristics at the different detection positions; for example, only radiation that lies in a specified segment of the energy spectrum is detected. In other words, the detector has different spectral sensitivities at the detection positions that are associated with the different strip-forming agents.

These and other advantages and features of the invention will be apparent from the following description of illustrative embodiments, considered along with the accompanying drawings.

BRIEF DESCRIPTION OF THE DRAWINGS

The invention will be explained in more detail below in the embodiment examples represented in the drawings, in which.

DESCRIPTION OF ILLUSTRATIVE EMBODIMENTS

Figure 1:
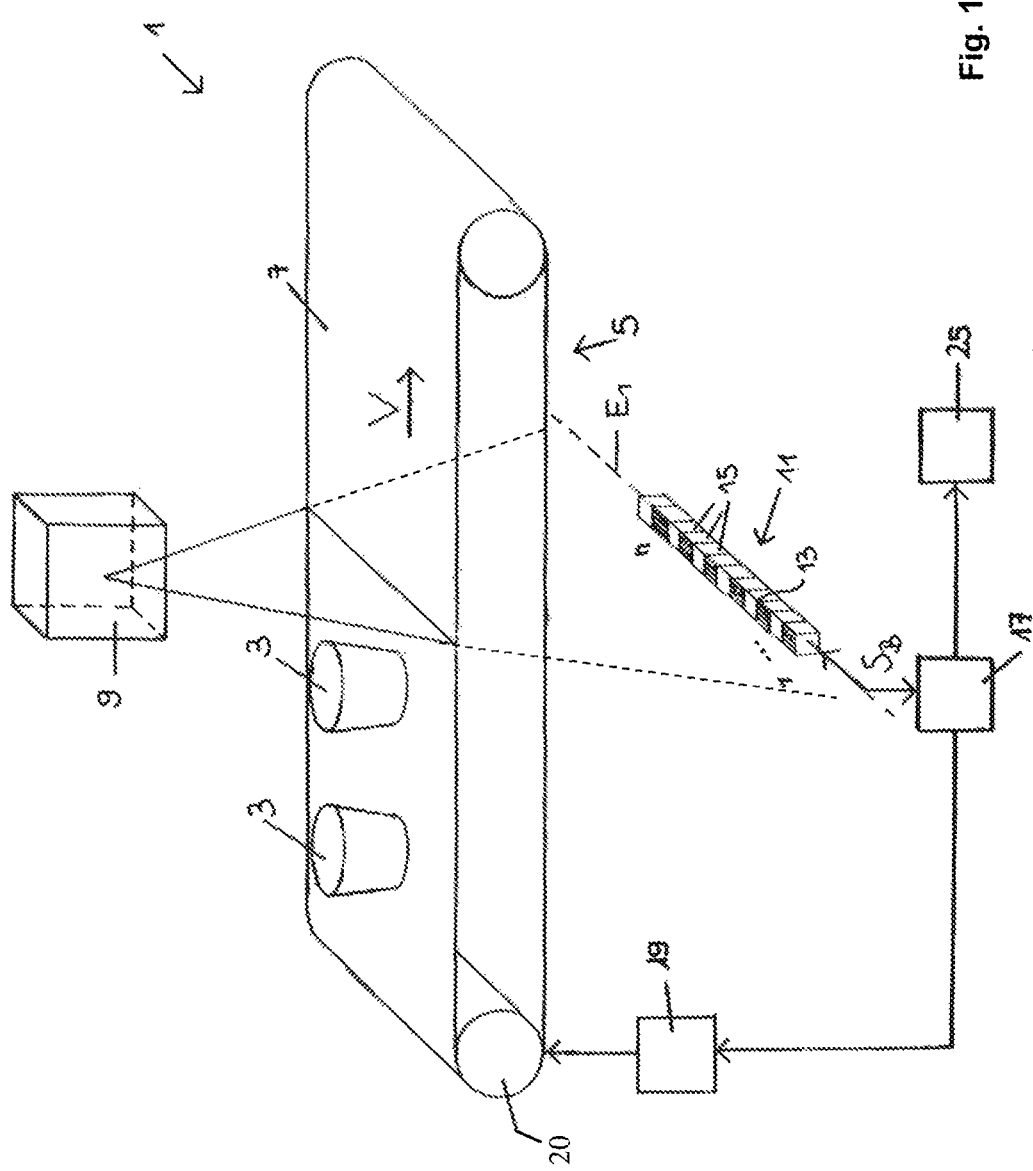
FIG. 1 shows a perspective schematic representation of the components of a device for detecting the structure of moving objects in accordance with one embodiment of the invention.

FIG. 1 shows the basic layout of a device 1 for detecting the structure of moving objects 3, which can be, for example, liquid or paste-like products, such as yogurt. The device 1 comprises a transport device 5, which in this embodiment example is designed as a belt conveyor. The belt conveyor 5 transports objects 3, which lie on the upper belt length of a conveyor belt 7 of belt conveyor 5, at a specified, preferably constant velocity. For clarity, the components of the device 1 are only shown schematically in FIG. 1, as necessary for understanding the invention.

An X-ray source 9 is arranged above the belt conveyor 5; it is designed so that the X-ray it generates essentially extends over the entire width of the conveyor belt 7. The X-ray generated by the X-ray source 9 covers at least one length in the direction of travel of the conveyor belt 7 that corresponds to the dimension of the sensitive region of an X-ray detector device 11 in this direction. The X-ray source 9 generates an X-ray with a broadband energy spectrum. In this way it is possible to detect X-ray images for different spectral portions of the radiation energy and thus to distinguish different materials or structures of the object 3 more or less clearly if said energy quanta with a specific energy content are better or worse absorbed. Through the compilation of the different images, better detectability of specific structures or materials or material regions can be achieved in correspondence with the known dual energy or multi-energy technique. Instead of a broadband spectrum, it is, of course, also possible for the X-ray source 9 to have at least two such spectral bands (dual energy method) or a plurality of such spectral bands (multi-energy method) that cover the energy regions with which the desired data in the irradiated object can be obtained.

The X-ray detector device 11 shown in FIG. 1 is a linear detector, whose sensor lines 13 extend in a straight line and perpendicular to the direction of travel v of the upper belt of the conveyor belt 7 and essentially parallel to the surface of the conveyor belt 7. The sensor line 13 has a number n, for example 1024, of sensors 15, which either convert the X-ray directly to an electrical signal or to an electromagnetic radiation (for example, visible light), which is generated by the X-ray by means of a converter in the form of a so-called scintillator arranged before the sensors 15. Said electromagnetic radiation generated by the scintillator (see below) can lie, for example, in the optical region, where in this connection the term "optical radiation" includes radiation in the infrared region or ultraviolet region.

The electrical image output signal $S_B$ of the X-ray detector device 11 is sent to an image data processing unit 17. The image data processing unit 17 can also control the X-ray detector device 11 in an appropriate way and, for example, determine the frequency with which the image data of a line of the entire sensor line 13 are read. In addition, the image data processing unit 17 can also clear the data present on the individual sensors 15 of the sensor line 13, which is stored, for example, as an electrical charge in each of the individual sensors 15, and in this way it can define the start of a new exposure interval. This is particularly advantageous when the X-ray source 9 generates a time-wise constant X-ray with a predetermined radiation power per unit area.

In this case, the information (electrical charge) stored in the sensors 15 of the sensor line 13 can be read in a simple way and sent as a preferably digitized value per sensor 15 to the image data processing unit 17. If the information content of the sensors 13 is read, for example, 10,000 times per second, a maximum exposure interval of 100 μsec results. In this interval, an electrical charge corresponding to the radiation energy received in said time interval can be generated in each of the sensors 15, on the active sensing surface of each sensor 15 (which can be made, for example, square). As noted above, for the amount of charge generated in a sensor 15, a corresponding digitized value can be generated, which can then be further processed by the image data processing unit 17. The analog-digital converter unit needed for this (not shown) is preferably provided in the X-ray detection device 11.

The sampling rate that can be achieved by means of the X-ray detector device 11 also determines the maximum possible velocity v for the travel of the objects 3 on the conveyor belt 7. If the conveyor belt 7 is operated, for example, at a velocity of 3 m/sec and the sampling rate is 10,000 sec$^{-1}$, a spatial sampling interval of 300 μm results. The maximum spatial resolution in the direction of travel is determined by the velocity and the maximum sampling rate. If the spatial resolution in the direction of travel should be variable, the image data processing unit 17 can control a drive unit 19 of the transport device 5 so that the desired, preferably constant, transport velocity v and/or the desired sampling rate results. As can be seen from FIG. 1, the drive unit 19 of the transport device 5 controls a roller 20 driven by a controllable motor (not shown) so that the desired transport velocity v is achieved.

From the image data of the sequentially sampled line data sent to it, the image data processing unit 17 can generate a complete image, which comprises the digital image data. The image data processing unit can be designed so that the first and last line data of an image associated is automatically detected or the relevant line number is generated. In other words, from the image data signal $S_B$ sent to it, the image data processing unit 17 can automatically detect when the leading edge of an object to be detected has been detected and when its end is reached. Of course, the beginning and end of a complete image can also be recognized by a separate sensor (not shown), which is designed, for example, as a photoelectric sensor, and which detects the leading edge or the trailing edge of an object that is to be detected. The photoelectric sensor can also be provided a certain distance in front of the detection line in which the sensor line 13 is arranged. This results in a certain lead time or lag time for the complete image, in the central region of which the object 3 is detected.

Since the dual energy method or multi-energy method is to be used in accordance with the invention to detect the structure of the objects 3, two or more different types of detection positions are defined along the detection line of the sensor line 13. These detection positions are indicated in FIG. 1 for two types of detection positions by the respective unshaded and shaded rectangles of the sensor line 13. They are designated as $p_1$ to $p_n$. The different types of detection positions $p_1$ to $p_n$ differ in that the X-ray detection device 11 has different spectral detector sensitivities at each of these detection positions. For example, at the detection positions of the sensor line 13 that are shown as unshaded rectangles, the X-ray detection device 11 can be designed so that the entire spectrum (energy spectrum) that is generated by the X-ray source 9 is detected unfiltered. The detection positions $p_1$ to $p_n$ shown as shaded rectangles can be designed so that an edge filter characteristic, for example a high pass characteristic, is realized here for the spectral sensitivity (energy spectrum). For example, here radiation quanta with a lower energy than established by a given filter edge can be suppressed or filtered out. Thus, at these shaded detection positions, only X-ray quanta are detected that exceed a certain energy threshold. The detection positions $p_1$ to $p_n$ of a sensor line can, looking at their geometric dimension, each correspond with the geometric dimension of the sensitive area of one sensor 15. However, it is of course also possible that the geometric dimension of one detection position $p_i$ (i=1 . . . n) is realized by a plurality of sensors 15 or their active sensitive area.

Thus, the image data processing unit 17 can extract two strip-shaped images from the image data signal $S_B$ sent to it, where the one image is determined by the unshaded detection positions and the other image by the shaded detection positions of the X-ray detection device 11 or by the sensors 15 that are associated with each of these detection positions.

The different types of detection positions $p_1$ to $p_n$ can be realized in different ways. An edge filter characteristic described above can, for example, be achieved through the use of filter materials of different densities. Examples for this are given in CN 101455573 A. The planar strip spatial filter described in said document for a planar sensor must, of course, for the application represented in FIG. 1 of this description, have strips that are only so long that they extend over the geometric dimension of the detection positions in the direction of travel.

It should be noted again at this point that, for realization of a multi-energy method, of course, a strip filter with a corresponding number of types of strip areas or regions with different filter characteristics must be provided in order to be able to obtain a corresponding number of images that each contain different data.

Not only edge filters, but rather any filters that generate an advantageous spectrum (with an advantageous spectral progression), can be used as filters.

Figure 2:
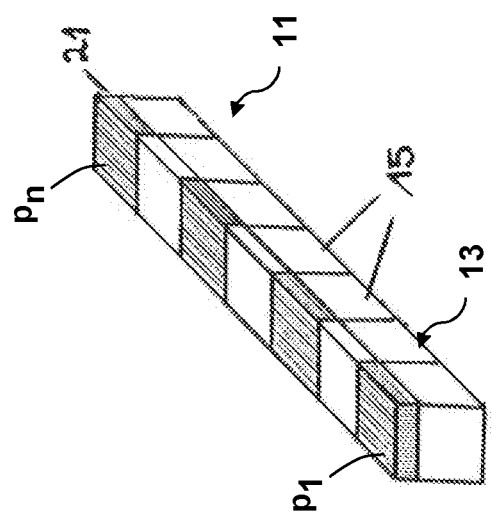
FIG. 2 shows a perspective, schematic representation of a first line-shaped embodiment of the X-ray detector device in FIG. 1 with a strip spatial filter.

One such strip filter with two different types of strip areas or regions is shown in FIG. 2 for the sensor line 13 (as in FIG. 1) as a filter layer 21 that is applied directly to the individual radiation-sensitive sensors 15 (for direct detection of X-rays). The filter layer 21 has the desired different spectral absorption properties or filter properties in the respective unshaded and shaded detection positions. For example, the filter layer 21 in the shaded regions (detection positions) can be made of a plastic and in the unshaded regions of copper, where copper here serves as an edge filter with high pass effect, i.e., only those radiation quanta whose energy is greater than a predetermined limit energy are transmitted.

The filter layer can, for example, be made so that first a plastic layer, and on top of that a copper layer, are applied to the sensors 15. Then the copper layer can be removed from the unshaded detection positions, for example etched away.

Of course, the filter layer 21 can also be introduced as separate filter components of the X-ray detection device 11 in the radiation path between the irradiated object 3 and the sensors 15 of the X-ray detection device 11. However, in this case, an exact positioning and alignment of the detection positions defined by the filter relative to the sensors must be ensured.

According to another embodiment, the X-ray detection device can also be designed so that individual sensors have inherently different spectral detector characteristics. To be sure, such a detector can be made only at clearly greater expense.

Since it is very important for industrial applications that the corresponding devices for detection of the structure of moving objects be able to be made at the lowest possible cost, it is expedient to use simple and inexpensive line detectors, which are available in long lengths and with high resolution at low cost, and to combine them with an appropriate filter layer, where the filter layer can either be applied directly to the surface of the sensors or, as described above, employed as a separate component.

Figure 3:
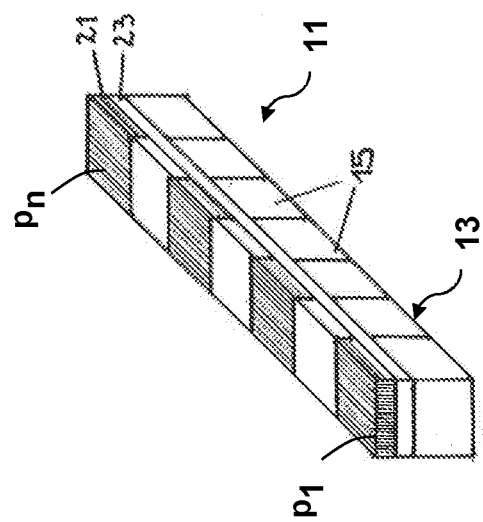
FIG. 3 shows another perspective schematic representation of a second line-shaped embodiment of the X-ray detector device in FIG. 1 with a strip spatial filter and a scintillator.

Since inexpensive line detectors for detection of electromagnetic radiation in the optical region are available, it is expedient, as shown in FIG. 3, to use in addition to the filter layer 21, a scintillator layer 23, which is provided between the filter layer 21 and the detector surface of the sensors 15. The scintillator layer 23 converts the portions of the incident X-ray transmitted through the filter layer 21 to an electromagnetic radiation in the optical spectrum, which can then be detected by the detectors 15. A simple and inexpensive X-ray detector can thus be made in this way.

According to one embodiment, the filter and the scintillator can also be designed to be uncoupled from the sensor as a unit. With this, it is possible to retrofit appropriate traditional X-ray detectors, for example traditional line cameras for X-rays, to a detector unit for a device in accordance with the invention. Moreover, such a separate unit can be adjusted highly accurately to the radiation path of the X-ray sensors with simple means. For example, the unit can have position markers (for example, position markers that can be irradiated with light in the visible spectrum outside of the filter region), with which the unit can be adjusted easily and precisely relative to the sensors using visible light. A simple camera for visible light, which clearly has higher resolution than the X-ray sensors, can be used for adjustments.

The image data processing unit 17 can, as is substantially known, calculate an output image from the partial images determined by it, to each of which the different types of preferably alternatingly arranged detection positions are associated. For this, values for the image data of the relevant partial image at the positions of the other partial image can be determined from the image data of the partial images by appropriate mathematical methods, for example interpolation methods or by using a fast Fourier transform. At these positions, the image data of the two images can then be combined in each case by a sign-dependent weighted addition. In this way, certain structures of objects to be investigated can be better distinguished in the output image.

Of course, it is also possible that the image data of all of the partial images are used in order to calculate the pertinent image data at given positions (within the line) by a suitable mathematical method. Then again, a weighted addition can take place at these positions.

The line by line determined output images can then be combined into a complete output image, which contains the complete object 3 (or a predetermined section). Of course, a calculation of image data at any intermediate positions can take place in the sampling in the direction of travel.

The image data processing unit 17 can send the line images or the entire output image to a subordinate unit 25, where said subordinate unit 25 can also be an indicator unit for the entire output image and/or the individual partial images (before they are superimposed). The image data processing unit 17 can also test the partial output images or the entire output image by means of the measured and calculated image data. For example, the output image can be tested for problematic structures with pattern recognition means. Thus, for example, impermissible solids or solid bodies in liquid or paste-like products such as yogurt could be recognized. Of course, any structures could be investigated with this method for certain structural properties.

Instead of or in addition to a computer evaluation of the output images, it is also possible for there to be a visual check by an operator of the relevant device. It is noted above that an indicator unit (not shown) can be provided for this. Such an embodiment can be used, for example, for baggage analysis at airports.

Figure 4:
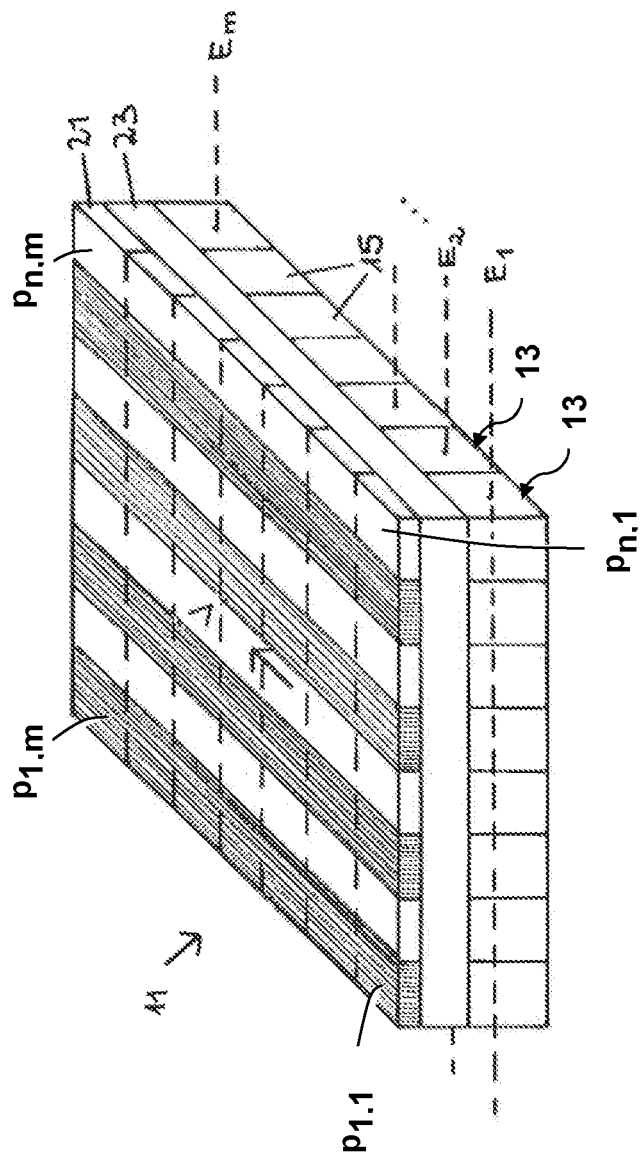
FIG. 4 shows a perspective schematic representation of a matrix-shaped embodiment for an X-ray detector device in FIG. 1 with a strip spatial filter and a scintillator.

FIG. 4 shows a schematic perspective view of another variation of an X-ray detector device 11. Again, it consists of a plurality of sensors 15, but in this case they are not arranged as just one line, but rather in the form of a plurality of or multiple lines. Each sensor line 13 runs along an associated detection line $E_1, E_2, \ldots, E_m$. Each sensor line 13 further has a number n of sensors 15, so that in this embodiment example there is a sensor matrix or a matrix of detection positions $p_{i,j}$ of dimension n×m (i=1, ..., n; j=1, ..., m). Of course, the individual sensor lines do not have to be immediately adjacent to each other, but rather can be arranged with a predetermined spacing.

Again, a scintillator layer 23 is provided over the sensor lines 13. On the scintillator layer 23 is provided a filter layer 21, which has a strip-shaped structure. The constant-width strip runs parallel to the direction of travel of the objects 3, i.e., perpendicular to the sensor lines 13 or their detection lines $E_1$ through $E_m$. Thus, the X-ray detector device 11 in accordance with FIG. 4 can generate via a number of m X-ray detector devices 11 or sensor lines 13 arranged one immediately behind the other, as was described for the embodiment in FIG. 1. The reading of the image data of the X-ray detector device 11 as in FIG. 4 can again take place line by line. A corresponding image data signal can be generated for each individual sensor line, so that all m image data signals can be sent in parallel to the image data processing unit. However, if the number of sensor lines is too large, groups of sensor lines 13 can be connected together in series with respect to the transfer of image data information to the image data processing unit 17, where only one image data signal is generated for each group.

With an X-ray detector device 11 as in FIG. 4, a larger segment of the imaged object 3 or even the entire object can be registered at the same time. If only a segment of the object is detected each time, the complete image can be composed by overlapping a plurality of partial images in the direction of travel. The partial images can in this case also be acquired in overlapping form and are not correspondingly compiled until the generation of the complete image. This can take place by detecting certain partial structures or the external geometry that are contained in successive partial images.

The partial images associated with the different spectral energy regions can be calculated in the corresponding way as was explained previously in connection with the embodiment as in FIGS. 1 to 3. The X-ray detector device 11 as in FIG. 4, of course, can also be made in other variations. For example, the strip filter 21 and/or the scintillator layer 23 can be positioned as independent components in the radiation path. In this regard, one should refer to the variations described above in connection with the X-ray detection device 11 as in FIGS. 1 to 3. Of course, this also applies to the variations in which the sensors 15 each already have a different spectral detector sensitivity.

Also conceivable would be a variant in which the scintillator layer has a different spectral characteristic along each detection line in correspondence with the detection positions, so that the partial images result from the fact that in the one detection position, the scintillator layer is designed so that a first segment of the X-ray spectrum is converted to a detectable optical radiation, while in the other detection positions, a different spectral segment is converted to a detectable optical radiation.

The X-ray detector device 11 as in FIG. 4, which includes m detector lines, can also be designed so that the amount of charge generated during a specific exposure interval by the sensors of a specific sensor line 13 is transferred at the end of each relevant time interval to the next sensor line in the direction of travel of the object or to the relevant sensors of the same gap. During the next time interval, additional charge is added to this transferred charge of the sensors to this sensor line 13 in correspondence with the X-ray detected during said exposure phase. If the ratio of the spacing of the detection lines in the direction of travel (an equidistant distribution of sensor lines is assumed) and the exposure phase or the constant length of the exposure interval time, which were constant in each case (after the charge at the next sensor line 13 in each case is added further), corresponds to the travel velocity v of the object on the transport device 5, the charge generated in each sensor line in the relevant sensors 15 will correspond in each case to the X-ray that passes through the same, an essentially vertical "slice" of the object that is to be registered (i.e., on essentially the same path). In this way, an m-fold "exposure" is achieved, through which a drastically improved image signal results. This method is called the TDI (Timing Delay Integration) method.

In this case, in accordance with FIG. 4, only the image signal of the last line of the X-ray detection device 11 in the direction of travel must be read and sent as image signal to the image data processing unit 17. This unit can then process this signal further in exactly the same way as explained above in the case of the embodiment in accordance with FIG. 1.

The combination of the TDI method and the use of a strip filter as spatial filter results in an extremely simple and inexpensive variation for detecting the structure of a moving object by means of irradiation of the object with X-rays.

Figure 5:
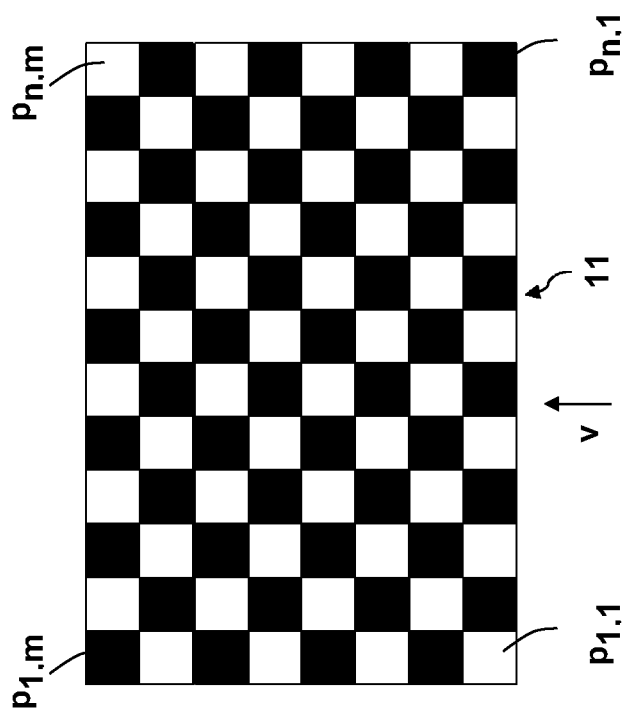
FIG. 5 shows a schematic top view of another matrix-shaped embodiment for an X-ray detector device in FIG. 1.

FIG. 5 shows a top view of an X-ray detector device 11, which, like the X-ray detector device 11 in FIG. 4, has two types of detection positions $p_{i,j}$ (i=1, ..., n; j=1, ..., m) arranged in a matrix shape, each of which is symbolized by unshaded or shaded squares. However, in contrast to the embodiment in FIG. 4, the detection positions here are not strip-shaped (with a long direction of the strips in the direction of travel), but they are arranged in a checkerboard pattern, where the axes or main directions of the checkerboard pattern (i.e., the directions of the strips with alternating types of detection positions) run transverse to the direction of travel (and at the same time essentially perpendicular to the irradiation direction), or they run in the direction of travel.

Compared to the embodiment in FIG. 4, this produces the advantage that for calculation of the value at a detection position at which no value is detected for the relevant partial image, not only can adjacent detected values of the same detection line be utilized, but detected values that lie adjacent in the direction of travel can also be employed. For example, to calculate the value of a partial image at the detection position $p_{i,j}$ (at which no value was detected for the relevant partial image, since this detection position is associated with the other of the two partial images), the values of the detection positions $p_{i-1,j}$ and $p_{i+1,j}$ (i.e., the adjacent values detected in the relevant detection line) and the values of the detection positions $p_{i,j-1}$, $p_{i,j+1}$ (i.e., the adjacent values detected in the direction of travel) are employed. Of course, any other two-dimensional calculation method (for example, the two-dimensional discrete Fourier transform) can also be used for such a calculation. This embodiment in accordance with FIG. 5 is also especially suitable for static detection of an object 3, i.e., a two-dimensional detection of the object 3 in resting state (velocity equal to zero) is carried out.

It is also possible to use the just described TDI method when using such an X-ray detector device. However, in this case for the integration or summation of the detected values at the positions of the relevant partial images that are detected in a sampling position of the object 3, in each case two lines (or detection positions in the direction of travel) or a whole number multiple thereof must be "pushed forward."

Only through this can one ensure that only values that are detected at the same type of detection position are added per partial image.

The use of a separate storage device, which can be called the background storage device, is recommended for the "pushing forward" of partial images by two or more lines or detection positions. A conventional TDI sensor, in which the charge of a pixel representing the relevant partial image (i.e., in a detection position) is sent forward to the following pixel in the direction of travel of the object 3 or the relevant detection position, can no longer be advantageously used here. Since if continuous radiation were used, the detection result for a partial image would be distorted when the charge representing the partial image or of the data representing the partial image would appear—even if only for a very brief time—at a detection position at which a different partial image is detected. It is therefore advantageous to read out the partial image data or the relevant charges after each (individual) detection operation in the background storage device and to shift them back into the relevant "forward shifted" detection positions via the detour through the background storage device. Alternatively, the integration of the individual values per partial image can also take place in the background storage device, where in this case the shifting by 2n lines must be taken into account in the readout of the background storage device.

Figure 6:
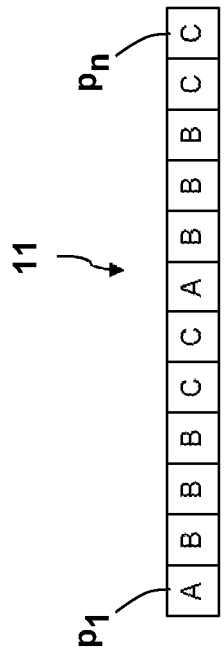
FIG. 6 shows a schematic top view of another line-shaped embodiment for an X-ray detector device in FIG. 1 with three types of detection positions.
Figure 7:
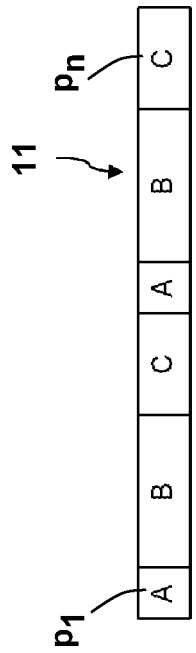
FIG. 7 shows a schematic top view of yet another line-shaped embodiment for an X-ray detector device in FIG. 1 with three types of detection positions.

FIGS. 6 and 7 each show a schematic top view of detection positions arranged in a respective line shape or line-shaped X-ray detector device 11, where three different types of detection positions are used, designated as A, B, and C.

In the variation in FIG. 6, the detection positions of different types are equal in area to each other and can be realized by identical sensors 15, which are combined with different types of filters or filter layers 21 and/or scintillators or scintillator layers 23. As can be seen from FIG. 6, the order of the types of detection positions can be selected as desired. It is not absolutely necessary that a strictly alternating sequence (ABCABC) be maintained. Rather, this structure can be matched to the relevant needs.

The variant in FIG. 7 shows that the width of the detection positions $p_1$ to $p_n$ along a detection line can also be selected through the use of sensors 15 of different widths and/or through the use of areas of different widths (strips in the direction of travel) of filters or filter layers 21 and/or scintillators or scintillator layers 23.

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described preferred embodiments are intended to illustrate the principles of the invention, but not to limit the scope of the invention. Various other embodiments and modifications to these preferred embodiments may be made by those skilled in the art without departing from the scope of the present invention.

LIST OF REFERENCE NUMBERS

1 Device for detection of the structure of moving objects
3 Object
5 Transport device/belt conveyor
7 Conveyor belt
9 X-ray source
11 X-ray detector device
13 Sensor line
15 Sensors of sensor line
17 Image data processing unit
19 Drive unit
20 Roller
21 Filter layer
23 Scintillator layer
25 Subordinate unit
$p_i$ Detection position (i=1 . . . n)
$p_{i,j}$ Detection position (i=1 . . . n; j=1 . . . m)
$S_B$ Image data signal
V Travel velocity of the object

The invention claimed is:

1. A method of producing an image for use in detecting the structure of moving objects, the method including:
(a) irradiating an object with X-ray radiation as the object moves along a direction of travel;
(b) for each of multiple sampling positions of the object in the direction of travel, detecting the radiation along a detection line extending transverse to the direction of travel, where a plurality of discrete first detection positions along the detection line detect a first spectral segment of the radiation and a plurality of discrete second detection positions along the detection line detect a second spectral segment of the radiation different from the first spectral segment of the radiation, the first and second detection positions being interleaved with each other along the detection line;
(c) detecting the radiation along at least one additional detection line extending transverse to the direction of travel and having a specified spacing with respect to the detection line in the direction of travel, where a plurality of discrete first detection positions along the at least one additional detection line detect the first spectral segment of the radiation and a plurality of discrete second detection positions along the at least one additional detection line detect the second spectral segment of the radiation, the first and second detection positions of the at least one additional detection line being arranged in the same configuration as the first and second detection positions of the detection line, and wherein the detecting the radiation along the detection line and the at least one additional detection line is performed in a time-shifted manner;
(d) converting the detected radiation to image data and adding together the image data from the detection line and the at least one additional detection line to produce, for each sampling position, a first partial image for the first spectral segment of the radiation and a second partial image for the second spectral segment of the radiation, the first partial image being produced based on the radiation detected at the first detection positions of the detection line and the at least one additional detection line, and the second partial image being produced based on the radiation detected at the second detection positions of the detection line and the at least one additional detection line; and
(e) arithmetically combining the first partial image and the second partial image into a partial output image in order to improve detectability of predetermined characteristics of the structure of the object.

2. The method of claim 1 further including combining the partial output image for one sampling position with the partial output image for each other sampling position to produce an output image.

3. The method of claim 1 wherein the detection positions along the detection line for a respective partial image are equidistant and spaced apart so that a structure of the object which has a predetermined minimum dimension transverse to the direction of travel extends along the detection line over at least two adjacent detection positions for that partial image.

4. The method of claim 1 wherein the sampling positions in the direction of travel of the object are selected to be equidistant and spaced apart so that a structure of the object which has a predetermined minimum dimension in the direction of travel extends over at least two sampling positions.

5. The method of claim 1 further including calculating, using a specified transformation procedure, a value for partial image data at an area along the detection line for one partial image from the detected radiation at adjacent detection positions for the other partial image.

6. The method of claim 1 further including testing each partial output image, or a complete output image formed from combining the partial output images, or specified segments of the complete output image for the presence of problematic characteristics that are to be detected.

7. An apparatus for detecting the structure of moving objects, the apparatus including:
(a) a transport device operable to move an object to be detected along a direction of travel;
(b) an X-ray source aimed to irradiate the object as it travels along the direction of travel;
(c) an X-ray detector device providing a detection line and at least one additional detection line having a predetermined spacing with respect to each other in the direction of travel, the detection line and the at least one addition detection line each extending transversely across the direction of travel and each including a respective plurality of discrete first detection positions adapted to detect a first spectral segment of the radiation and a respective plurality of discrete second detection positions adapted to detect a second spectral segment of the radiation different from the first spectral segment of the radiation, the first and second detection positions of the detection line being interleaved with each other along the detection line and the first and second detection positions of the at least one additional detection line being interleaved with each other along the at least one additional detection line in the same configuration as the detection positions of the detection line, and producing for a respective sampling position of the object along the direction of travel, a first partial image for the first spectral segment of the radiation and a second partial image for the second spectral segment of the radiation, the first partial image being produced based on the radiation detected at the first detection positions of the detection line and the at least one additional detection line, and the second partial image being produced based on the radiation detected at the second detection positions of the detection line and the at least one additional detection line; and
(d) an image data processing unit adapted to receive and combine partial image data for the first partial image and partial image data for the second partial image into a partial output image providing improved detectability with respect to predetermined characteristics of the structure of the object and
(e) wherein the X-ray detector device detects the X-rays at the detection line and the at least one additional detection line in a time-shifted manner so that the detection line and the at least one additional detection line detect radiation that has penetrated the same portion of the object.

8. The apparatus of claim 7 wherein the image data processing unit is also operable to combine the partial output image for each different sampling position into an output image.

9. The apparatus of claim 7 wherein the detection positions along the detection line for a respective partial image are equidistant and spaced apart so that a structure of the object which has a predetermined minimum dimension transverse to the direction of travel extends along the detection line over at least two adjacent detection positions for that partial image.

10. The apparatus of claim 7 wherein the sampling positions in the direction of travel of the object are selected to be equidistant and spaced apart so that a structure of the object which has a predetermined minimum dimension in the direction of travel extends over at least two sampling positions.

11. The apparatus of claim 7 wherein the image data processing unit applies a specified transformation procedure to calculate a value for partial image data at an area along the detection line for one partial image from the detected radiation at adjacent detection positions for the other partial image.

12. The apparatus of claim 7 wherein the image data processing unit tests each partial output image, or a complete output image formed from combining the partial output images, or predetermined segments of the output image for the presence of object characteristics that are to be detected.

13. The apparatus of claim 7 wherein the X-ray detector device includes a series of radiation sensors arranged along the detection line and a corresponding series of radiation sensors arranged along the at least one additional detection line and wherein each detection position along the detection line and the at least one additional detection line is formed by one or more of the radiation sensors.

14. The apparatus of claim 13 wherein the radiation sensors at the first detection positions or the radiation sensors at the second detection positions have a sensitivity that corresponds to the respective spectral segment of the X-rays generated by the X-ray source.

15. The apparatus of claim 13 wherein:
(a) the X-ray detector device includes a spatial filter arranged between the object and the radiation sensors for filtering the X-ray radiation to be detected, the spatial filter having a strip structure with a set of strips of constant width for each of the first partial image and the second partial image, the set of strips for the respective partial image having a filter characteristic associated with that partial image in order to pass the relevant spectral segment of the X-ray; and
(b) the width of the strips corresponds to the dimension and position of the associated detection positions along the detection line and the at least one additional detection line.

16. The apparatus of claim 15 wherein the spatial filter is made integral with the radiation sensors of the X-ray detector device.

* * * * *